United States Patent [19]

Forbes et al.

[11] Patent Number: 4,802,626
[45] Date of Patent: Feb. 7, 1989

[54] MOLDED SCENT IMPREGNATED DEVICES

[75] Inventors: David R. Forbes; Carman S. Forbes, both of Hiawatha, Iowa

[73] Assignee: Hunter's Specialties, Inc., Cedar Rapids, Iowa

[21] Appl. No.: 943,958

[22] Filed: Dec. 22, 1986

[51] Int. Cl.⁴ .............................................. A61L 9/00
[52] U.S. Cl. ........................................ 239/36; 239/54; 239/60; 248/339; 428/905
[58] Field of Search ...................... 239/37, 53, 54, 55, 239/56, 57, 60, 36; 428/905; 248/301, 304, 339

[56] References Cited

U.S. PATENT DOCUMENTS

| | | | |
|---|---|---|---|
| 1,780,408 | 11/1930 | Smith | 239/55 |
| 2,120,204 | 6/1938 | Langhorst | 239/54 |
| 2,218,037 | 10/1940 | Duers et al. | 239/54 |
| 2,629,628 | 2/1953 | Vaillancourt . | |
| 2,988,284 | 6/1961 | Smith | 239/60 |
| 3,046,192 | 7/1962 | Bilyeu . | |
| 3,785,561 | 1/1974 | Confino et al. | 239/60 |
| 3,972,993 | 8/1976 | Kobayashi et al. . | |
| 3,994,439 | 11/1976 | Van Breen et al. | 239/54 |
| 4,160,335 | 7/1979 | Von Kohorn et al. . | |
| 4,229,415 | 10/1980 | Bryson | 239/57 |
| 4,302,899 | 12/1981 | DeHart . | |
| 4,526,320 | 7/1985 | Von Philipp et al. | 239/57 |

FOREIGN PATENT DOCUMENTS

| | | |
|---|---|---|
| 498302 | 12/1953 | Canada . |
| 2341938 | 3/1975 | Fed. Rep. of Germany . |
| 2088119 | 1/1972 | France . |
| 1056657 | 3/1986 | Japan . |

Primary Examiner—Andres Kashnikow
Assistant Examiner—Chris Trainor
Attorney, Agent, or Firm—Simmons, Perrine, Albright & Ellwood

[57] ABSTRACT

Small honeycombed devices, such as wafers, for hunting, trapping and other purposes are molded from plastic material impregnated with artificial simulations of natural scents or other scents such as insect repellants, attractants or insecticides, deodorants or deodorizers, or decorative and floral fragrances. Means may be included by which the devices can be removably stacked together to intensify a particular scent or to provide a combination of different scents and/or by which the devices can be suspended from a supporting object.

5 Claims, 1 Drawing Sheet

MOLDED SCENT IMPREGNATED DEVICES

BACKGROUND OF THE INVENTION

Hunters and trappers have long used various natural scents to attract game, just as others have long used various artificial repellants, attractants and insecticides against insects. Typical devices for attracting game include pads saturated with a liquid lure, such as animal urine, the pad being mounted in a small perforated container which is attached to the hunter or nearby foliage, as in U.S. Pat. Nos. 3,046,192 and 4,302,899, for example. In the case of insects similar devices have been used to repel them, as in U.S. Pat. Nos. 1,780,408 and 2,629,628, for example. U.S. Pat. No. 3,972,993 discloses an insecticide coated or impregnated sheet sandwiched between a pair of perforated sheets containing an insect attracting substance. A somewhat similar scheme is shown in U.S. Pat. No. 4,160,335 for controlling pests.

But especially in the case of the lures employed by hunters, the typical scent impregnated pads tend to be messy and of fairly limited effective duration. They require the hunter to carry a bottle or bottles of the scent or scents to be used which are subject to leakage, spill and the like with the consequent ruin of clothes, car seats, carpets, and so forth. The same demerits are also true of liquid insect repellants and insecticides applied to pads and the like. The laminated examples of insect lures and insecticides in U.S. Pat. Nos. 3,972,993 and 4,160,335 avoid the mess involved with liquids but lack the ability to disperse a scent well and/or to readily increase or decrease a particular scent or combine or interchange scents.

So the primary object of the present invention is to provide a scent device primarily for hunting and trapping but also adaptable to other uses, which device eliminates the deficiencies of prior devices and is much more adaptable to various needs and environments.

SUMMARY OF THE INVENTION

The invention's object and others are achieved by integrally molded, honeycombed structures of plastic material impregnated with one or more different scents. In one preferred form the scent devices comprise circular, honeycombed wafers which can be used separately or, if additionally fitted, can be removably stacked together to provide varying levels of scent intensity or a variety of different scents in a single stack. In wafer form especially, the devices are light and compact and a single wafer or a number of same can be attached to the person, to foliage, or to some other support by means of an optional hook of the same scent impregnated material attached to each wafer, or by a pin, string or the like through one of the honeycombed apertures. The honeycombed configuration of the devices, whether in wafer or other form, allows maximum air movement in and around all scented surfaces, as well as maximum surface area for aerobic scent dispersion, the scent molecules being transferred only into air currents and not lost by absorption into cloth or soil as is the case with current such devices.

For hunting and trapping purposes artificially simulated food scents such as "acorn", "fermented apple", and "peanut butter", or artificially simulated sex scents such as urine, musk and natural pheromones collected from whitetail does during the peak of their estrus cycle, are impregnated in the devices during their manufacture. For other employments, insect repellants, insecticides and attractants can be impregnated, as can deodorants and deodorizers and the like for household and similar applications or various fragrances for decorative and floral purposes. In short, the honeycombed, scent impregnated devices of the invention, though designed initially for hunting and trapping purposes, have a wide swath of possible uses.

Other and further features and advantages of the invention will become apparent from the drawings and more detailed description which follows.

DETAILED DESCRIPTION OF A PREFERRED EMBODIMENT

Figure 1:
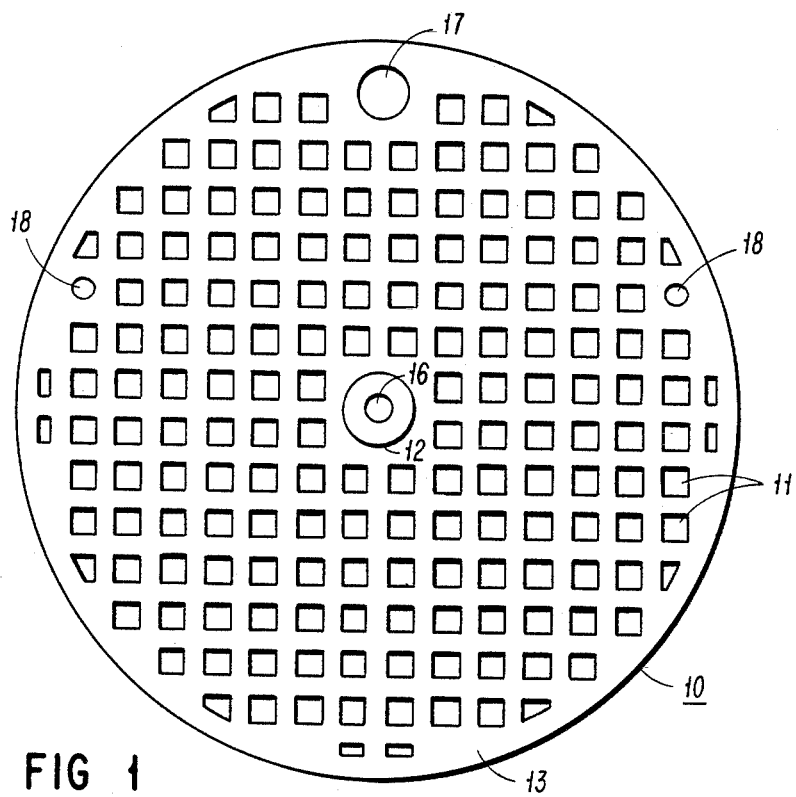
FIG. 1 is a plan view of a scent wafer incorporating the invention and including means for stacking the wafers together.
Figure 2:
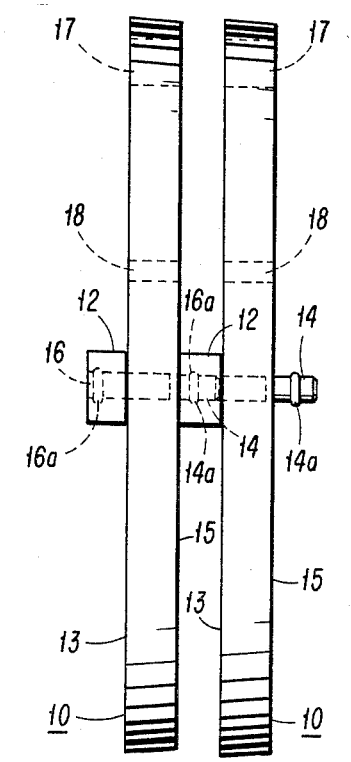
FIG. 2 is a side view of a pair of the wafers of FIG. 1 shown stacked together.
Figure 3:
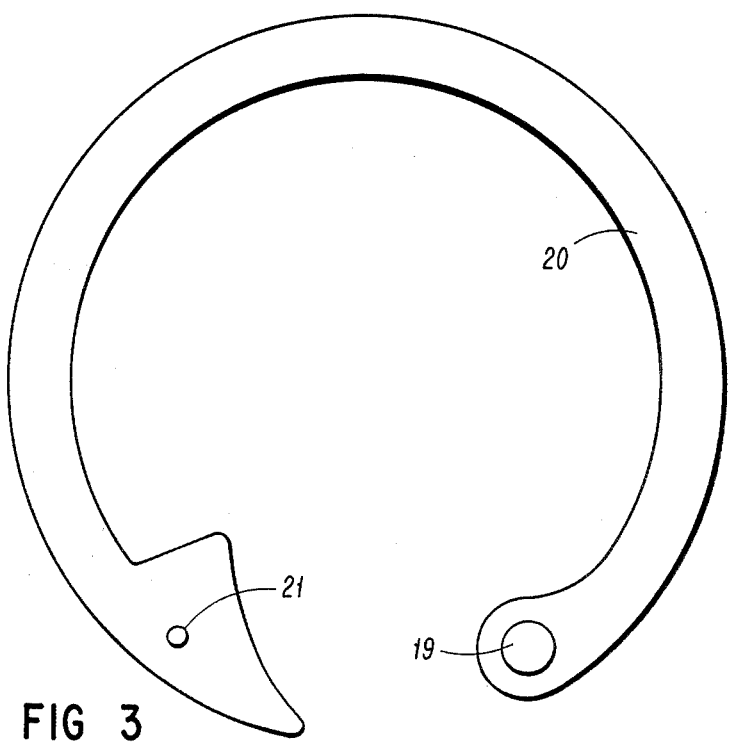
FIG. 3 is an enlarged plan view of a suspending hook for each wafer.
Figure 4:
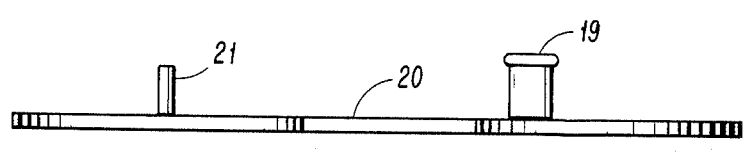
FIG. 4 is a side view of the hook of FIG. 3.
Figure 6:
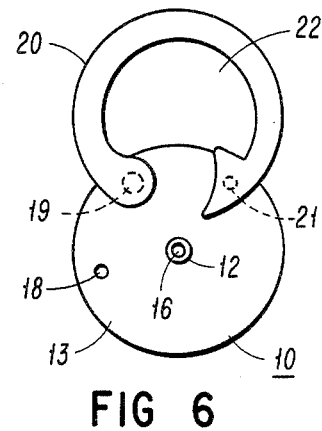
FIGS. 5 and 6 are plan views of a wafer with the hook attached and illustrating the folded and unfolded positions of the hook.
Figure 5:
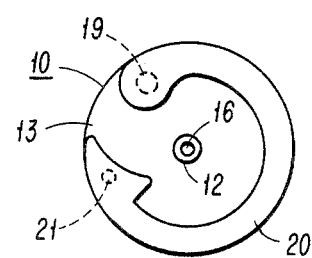

The wafer form of the invention, as noted, comprises a molded circular disc 10 honeycombed through at 11 and slightly tapered at the edges in order to assist removal of the discs 10 from the mold. The apertures 11 are similarly tapered for the same purpose and may of course be of any shape so long as their size and number permit maximum flow of air currents through the wafers. If the ability to stack the wafers together is desired, the center of each wafer may be provided with an integral axial boss 12 on one face 13 and an integral axial stud 14 on its opposite face 15. The disc 10 and boss 12 have an axial bore 16 which removably retains the stub 14 of an adjacent disc 10 so that the wafers can be stacked together as shown in FIG. 2. To assist retention of the stub 14 in the bore 16 the former is provided with a small integral collar 14a which snaps into a complementary recess 16a in the bore 16. If it is desired to equip the wafers with means to suspend them, the disc 10 can be provided with a bore 17, parallel to the axis of the disc 10 and just inboard of its edge, and a pair of parallel smaller bores 18 equally spaced circumferentially from the bore 17. The bore 17 pivotally anchors a headed stud 19 on and integral with one end of a thin, C-shaped molded hook 20 whose outer margin is congruent with that of the disc 10 when the hook 20 is stowed, as shown in FIG. 5, on the disc face 13. The other end of the hook 20 is also provided with a smaller integral stud 21 which frictionally engages one or the other of the bores 18 to retain the hook 20 in either its stowed position shown in FIG. 5 or in its operative position shown in FIG. 6. In the latter position the hook 20 defines an enclosed space 22 with the adjacent edge of the disc 10 so that the wafer can be hung from a suitable support.

The discs 10 and hook 20 are preferably molded of a low density polyethylene plastic containing ethyl vinyl acetate to render the plastic softer, flexible and more easily molded as well as enabling it to carry or "absorb" the scent better. The scents themselves are artificial simulations of natural scents and are achieved by identifying the chemical constituents and their proportions of each natural scent and then artificially reproducing those constituents and their combination to form an oleagineous liquid. The latter is then mixed in with the low density polyethylene and ethyl vinyl acetate and formed into solid "beads" which are supplied to the molder. The molder in turn tumbles together a 50—50 mixture of the "beads" and further low density polyethylene and 7% vinyl acetate by weight in granular form plus suitable coloring. The mixture is then introduced into the molding machinery and heated to about 280 F or less if possible under high pressure to produce the wafers and the hooks. In some cases where the scent is obnoxious—fox urine is a good example—it is best first to mold the wafers and hooks from a mixture of 50% low density polyethylene and 50% ethyl vinyl acetate and then to tumble them with the scent oil in a closed, dedicated container in order to avoid irreparable "contamination" of the molding machinery.

The wafer form of the invention is remarkably compact, commercial examples measuring two inches in diameter and one-eighth inch in thickness, the honeycombed perforations being each a nominal 0.078 inches square and effectively about 162 in number. They are presently marketed in groups of three enclosed in a small air-tight container for preservation and rejuvenation when not in use. In use it is the honeycombed structure of the wafers, which not only greatly increases their exposed area but also allows air flow through them, that appears chiefly responsible for their quite remarkable power in view of their small size to disperse a scent or scents over a wide area despite little air movement about the wafers. Non-honeycombed wafers would have to be of much larger dimensions, and thus not be nearly as handy and adaptable, in order to possess equal exposed area. Even then the larger wafers would not possess the important aspect of allowing air flow through as well as around them. After use the wafers return to full strength in the containers as new scent molecules push their way to the wafer surfaces. For hunting purposes two, three or even more wafers of the same scent can be used to provide varying scent intensities. For deer hunting usually one wafer is powerful enough to attract the animal but on calm days or in areas of low deer density two or three wafers may be better. Alternately, a number of wafers of one or more different scents can be used to provide a combination of scents. Excellent combinations for deer hunting, for example, are "moist forest soil" and "doe in estrus", or the latter and "peanut butter". Similar flexibility is available for wafers impregnated with an insecticide, an insect repellant or attractant, with a deodorizer or deodorant, or with various fragrances and the like.

In the hunting field the wafers, which for that purpose are produced in natural forest colors, can be placed in animal "scrapes", hung by their hooks on trees or other foliage, or mounted above the ground on sticks to catch air currents, or pinned to the hunter's clothing, and so forth. The wafers can even be attached to target arrows and shot to appropriate spots around tree stands without accompanying human odor. The latter technique is particularly beneficial in heavily hunted areas where the animals are especially cautious. A package of three wafers outperforms liquid scents, lasting an entire hunting season, whereas three to five bottles of liquid scents are normally required for a like time. Scents can be changed in a few moments if a different one appears more effective. Since the wafers are solid, in contrast to liquid scents there is no waste nor can they ruin clothing, car seats and carpets and the like through leakage. Scent quality and strength does not deteriorate or change during storage of the wafers in their containers. The scent is "sealed" in the wafers until they are removed for use so that they can be stored in the camp or at home with far less chance of odorizing either during storage. The wafers can be used in all weather conditions as, unlike liquid scents, they will not freeze or be diluted by rain, heavy dew or snow.

Though the present invention has been described in terms of a particular embodiment, being a best mode known of carrying out the invention, it is not limited to that embodiment alone. Other scent devices of honeycombed structure molded from scent impregnated material, whether or not of wafer form and whether stackable or not, are also deemed within the ambit of the invention. Hence, the following claims are to be read as encompassing all adaptations and modifications of the invention falling within its spirit and scope.

We claim:

1. A scent impregnated device having at least one two-faced wafer of molded material impregnated with a scent, wherein each wafer comprises a circular disc having a plurality of honeycombed perforations therethrough from face-to-face effective to allow air currents to flow therethrough from face-to-face, each of the wafer faces including attaching means disposed at the center thereof and molded integrally therewith for manually removably attaching a plurality of the wafers together in stacked, axially aligning and spaced relation to each other by first axially aligning the wafers, then moving the same along the axis and finally engaging the attaching means.

2. The wafer of claim 1 including a separate member attached thereto for suspending the wafer from a supporting object.

3. The wafer of claim 2 wherein the suspending member is also integrally molded from the scent impregnated material.

4. A scent impregnated device of claim 1, 2, or 3 wherein said at least one two faced wafer comprises a plurality of wafers removably attached together, and wherein the scent of at least one of the wafers differs from the scent of at least one of the other wafers.

5. The wafers of claim 4 wherein the attaching means comprise a stud extending axially from one face of the wafer and a boss extending axially from the other face of the wafer, the boss including an axially extending stud-receiving bore therein effective to removably engage the stud of another wafer.

* * * * *